United States Patent
Liu et al.

(10) Patent No.: US 10,585,049 B2
(45) Date of Patent: Mar. 10, 2020

(54) PROCESS-INDUCED EXCURSION CHARACTERIZATION

(71) Applicant: KLA-Tencor Corporation, Milpitas, CA (US)

(72) Inventors: Helen (Heng) Liu, Fremont, CA (US); Aye Aung, Milpitas, CA (US); GuoQing Zhang, Milpitas, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 16/273,876

(22) Filed: Feb. 12, 2019

(65) Prior Publication Data

US 2019/0277777 A1 Sep. 12, 2019

Related U.S. Application Data

(60) Provisional application No. 62/641,297, filed on Mar. 10, 2018.

(51) Int. Cl.
| | |
|---|---|
| *G01N 21/95* | (2006.01) |
| *G01N 21/956* | (2006.01) |
| *H01L 23/498* | (2006.01) |
| *G06F 17/50* | (2006.01) |

(52) U.S. Cl.
CPC ....... *G01N 21/9505* (2013.01); *G01N 21/956* (2013.01); *G06F 17/5068* (2013.01); *H01L 23/49838* (2013.01)

(58) Field of Classification Search
CPC .............. G01N 21/9505; G01N 21/956; G06F 17/5068; H01L 23/49838
See application file for complete search history.

(56) References Cited

U.S. PATENT DOCUMENTS

| | | | |
|---|---|---|---|
| 8,611,639 B2 * | 12/2013 | Kulkarni ............ | G01N 21/9501 382/145 |
| 2004/0122859 A1 | 6/2004 | Gavra et al. | |
| 2010/0067781 A1 | 3/2010 | Huet et al. | |
| 2013/0035877 A1 | 2/2013 | Kirk et al. | |
| 2015/0154746 A1 | 6/2015 | Zafar et al. | |
| 2015/0234000 A1 | 8/2015 | Butler et al. | |

OTHER PUBLICATIONS

International Search Report and Written Opinion dated Jun. 17, 2019 for PCT/US2019/021389.

\* cited by examiner

*Primary Examiner* — Seahvosh Nikmanesh
(74) *Attorney, Agent, or Firm* — Suiter Swantz pc llo

(57) ABSTRACT

A system includes a controller with one or more processors and memory configured to store one or more sets of program instructions. The one or more processors are configured to execute the one or more sets of program instructions. The one or more sets of program instructions are configured to cause the one or more processors to apply filtering to a semiconductor wafer map; separate the filtered semiconductor wafer map into a plurality of dies; generate a set of die comparison statistics for the plurality of dies; generate at least one excursion map by applying at least one inspection threshold to the set of die comparison statistics; and detect at least one excursion within the at least one excursion map.

28 Claims, 9 Drawing Sheets

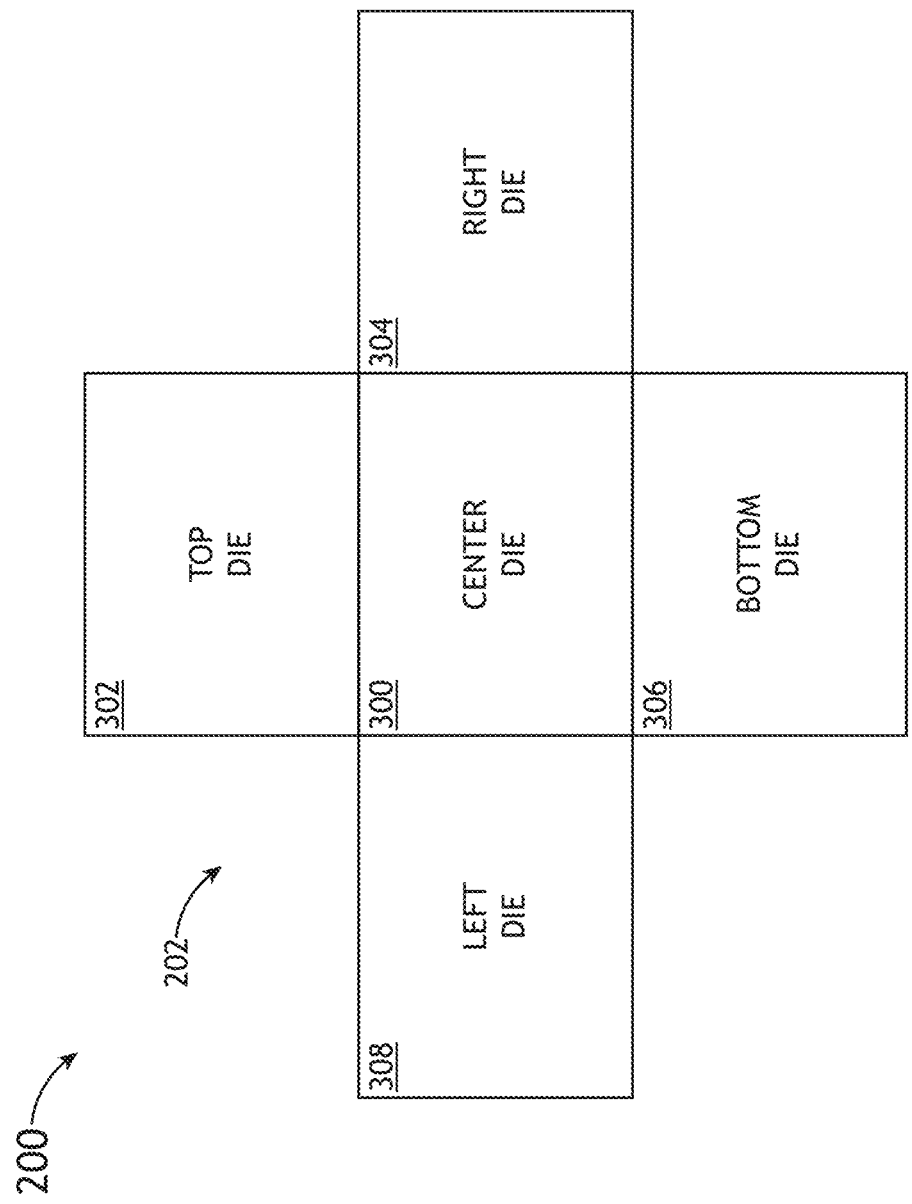

PROCESS-INDUCED EXCURSION CHARACTERIZATION

CROSS-REFERENCE TO RELATED APPLICATIONS

The present application claims the benefit under 35 U.S.C. § 119(e) of U.S. Provisional Patent Application Ser. No. 62/641,297, filed Mar. 10, 2018, titled PATTERN WAFER GEOMETRY DIE TO DIE INSPECTION, naming Helen Liu as inventor, which is incorporated herein by reference in the entirety.

TECHNICAL FIELD

The present invention generally relates to semiconductor device production and, more particularly, to process-induced excursion characterization.

BACKGROUND

The fabrication of semiconductor devices such as logic and memory devices typically includes processing a semiconductor device using a number of fabrication processes and characterization processes to form various features and multiple layers of the semiconductor device. Select fabrication processes utilize photomasks/reticles to print features on a semiconductor device such as a wafer. As semiconductor devices become smaller and smaller laterally and extended vertically, it becomes critical to develop enhanced characterization processes with increased sensitivity and throughput.

Excursions (e.g., a random and/or significant topography deviation by a fabrication process or fabrication tool from nominal specification) may cause the semiconductor devices to develop defects. Select characterization processes for locating excursions and/or defects include wafer geometry metrology processes (e.g., pattern wafer geometry (PWG) metrology, topography metrology, or the like) and wafer inspection processes (e.g., die-to-die inspection).

Wafer geometry metrology processes, however, may lose detailed information about the topography of the wafer surface, which may limit the issue-finding capability of full wafer topography. In addition, wafer inspection processes may not respond to z-height and/or surface geometry defects. As such, geometry-induced defects may not be solely covered by either wafer geometry metrology processes or wafer inspection processes.

Therefore, it would be advantageous to provide a system and method that cures the shortcomings described above.

SUMMARY

A system is disclosed, in accordance with one or more embodiments of the present disclosure. In one embodiment, the system includes a controller. In another embodiment, the controller includes one or more processors and memory configured to store one or more sets of program instructions. In another embodiment, the one or more processors are configured to execute the one or more sets of program instructions. In another embodiment, the one or more sets of program instructions are configured to cause the one or more processors to apply filtering to a semiconductor wafer map. In another embodiment, the one or more sets of program instructions are configured to cause the one or more processors to separate the filtered semiconductor wafer map into a plurality of dies. In another embodiment, the one or more sets of program instructions are configured to cause the one or more processors to generate a set of die comparison statistics for the plurality of dies. In another embodiment, the one or more sets of program instructions are configured to cause the one or more processors to generate at least one excursion map by applying at least one inspection threshold to the set of die comparison statistics. In another embodiment, the one or more sets of program instructions are configured to cause the one or more processors to detect at least one excursion within the at least one excursion map.

A system is disclosed, in accordance with one or more embodiments of the present disclosure. In one embodiment, the system includes a characterization tool. In another embodiment, the system includes a controller. In another embodiment, the controller includes one or more processors and memory configured to store one or more sets of program instructions. In another embodiment, the one or more processors are configured to execute the one or more sets of program instructions. In another embodiment, the one or more sets of program instructions are configured to cause the one or more processors to apply filtering to a semiconductor wafer map. In another embodiment, the one or more sets of program instructions are configured to cause the one or more processors to separate the filtered semiconductor wafer map into a plurality of dies. In another embodiment, the one or more sets of program instructions are configured to cause the one or more processors to generate a set of die comparison statistics for the plurality of dies. In another embodiment, the one or more sets of program instructions are configured to cause the one or more processors to generate at least one excursion map by applying at least one inspection threshold to the set of die comparison statistics. In another embodiment, the one or more sets of program instructions are configured to cause the one or more processors to detect at least one excursion within the at least one excursion map.

A method is disclosed, in accordance with one or more embodiments of the present disclosure. In one embodiment, the method may include, but is not limited to, applying filtering to a semiconductor wafer map. In another embodiment, the method may include, but is not limited to, separating the filtered semiconductor wafer map into a plurality of dies. In another embodiment, the method may include, but is not limited to, generating a set of die comparison statistics for the plurality of dies. In another embodiment, the method may include, but is not limited to, generating at least one excursion map by applying at least one inspection threshold to the set of die comparison statistics. In another embodiment, the method may include, but is not limited to, detecting at least one excursion within the at least one excursion map.

BRIEF DESCRIPTION OF THE DRAWINGS

The numerous advantages of the present disclosure may be better understood by those skilled in the art by reference to the accompanying figures in which:

FIG. 3A illustrates a simplified schematic view of semiconductor wafer dies defined within a semiconductor wafer map, in accordance with one or more embodiments of the present disclosure;

DETAILED DESCRIPTION OF THE INVENTION

Reference will now be made in detail to the subject matter disclosed, which is illustrated in the accompanying drawings.

Referring generally to FIGS. 1-6, a system and method for process-induced excursion characterization is disclosed, in accordance with one or more embodiments of the present disclosure.

Embodiments of the present disclosure are directed to process-induced excursion characterization. Embodiments of the present disclosure are also directed to improving the performance of characterization tools via control of characterization processes in response to excursions located by combining wafer geometry metrology processes with wafer inspection processes to promote an increased sensitivity and accuracy when detecting excursions caused by the fabrication processes. Embodiments of the present disclosure are also directed to improving the performance of fabrication tools via control of fabrication processes by adjusting the fabrication tools in response to excursions located by combining wafer geometry metrology processes with wafer inspection processes to promote an increased sensitivity and accuracy when detecting excursions caused by the fabrication processes.

FIGS. 1-4 generally illustrate a method for process-induced displacement characterization, in accordance with one or more embodiments of the present disclosure.

Figure 1:
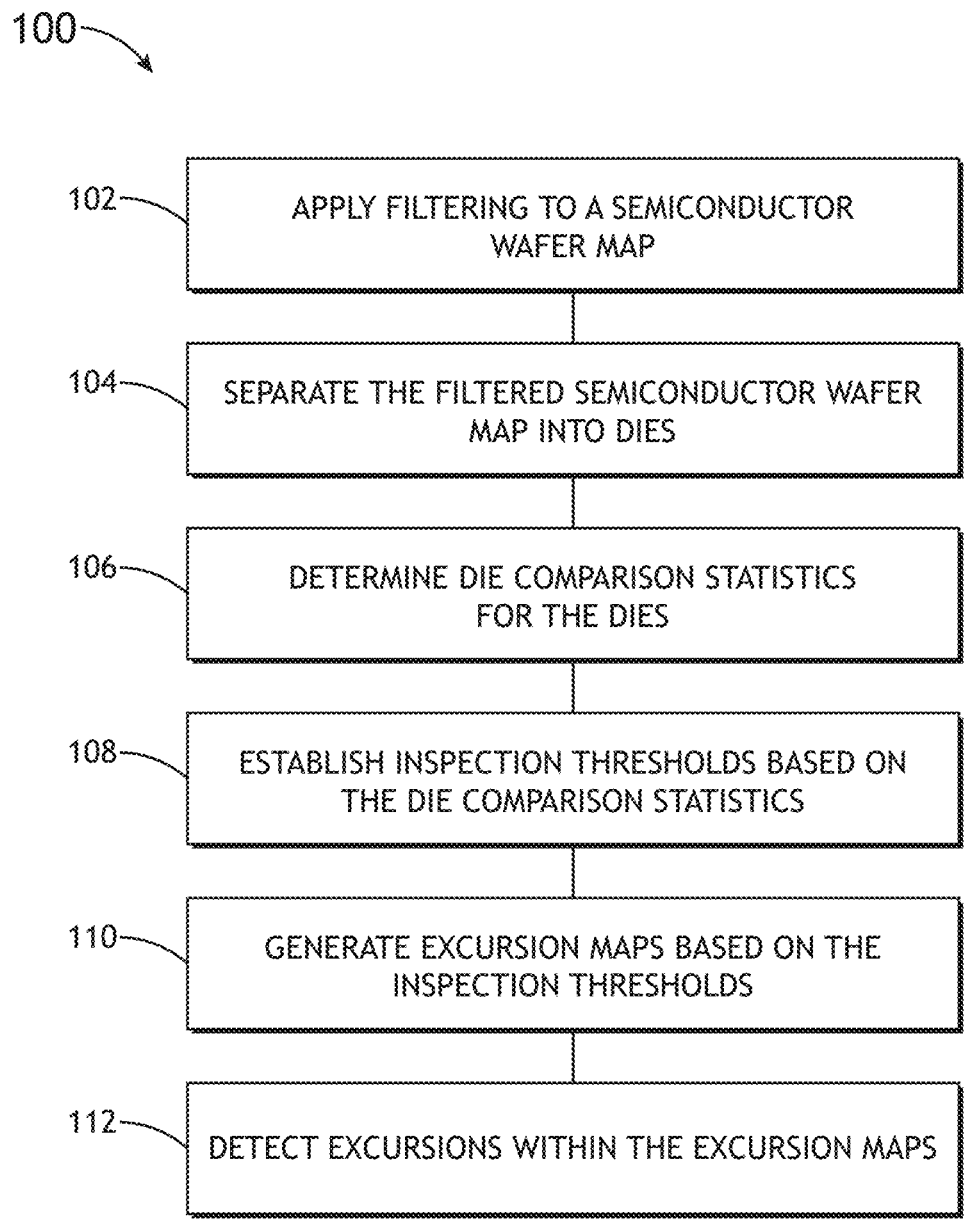
FIG. 1 illustrates a flow diagram of a method for process-induced excursion characterization, in accordance with one or more embodiments of the present disclosure.

FIG. 1 illustrates a method 100 for process-induced excursion characterization, in accordance with one or more embodiments of the present disclosure.

In a step 102, filtering is applied to a semiconductor wafer map. In one embodiment, the filtering may include applying one or more algorithms to derive one or more select die metrics from the semiconductor wafer map. In another embodiment, filtering is applied as set forth by a recipe for the semiconductor wafer.

Figure 2A:
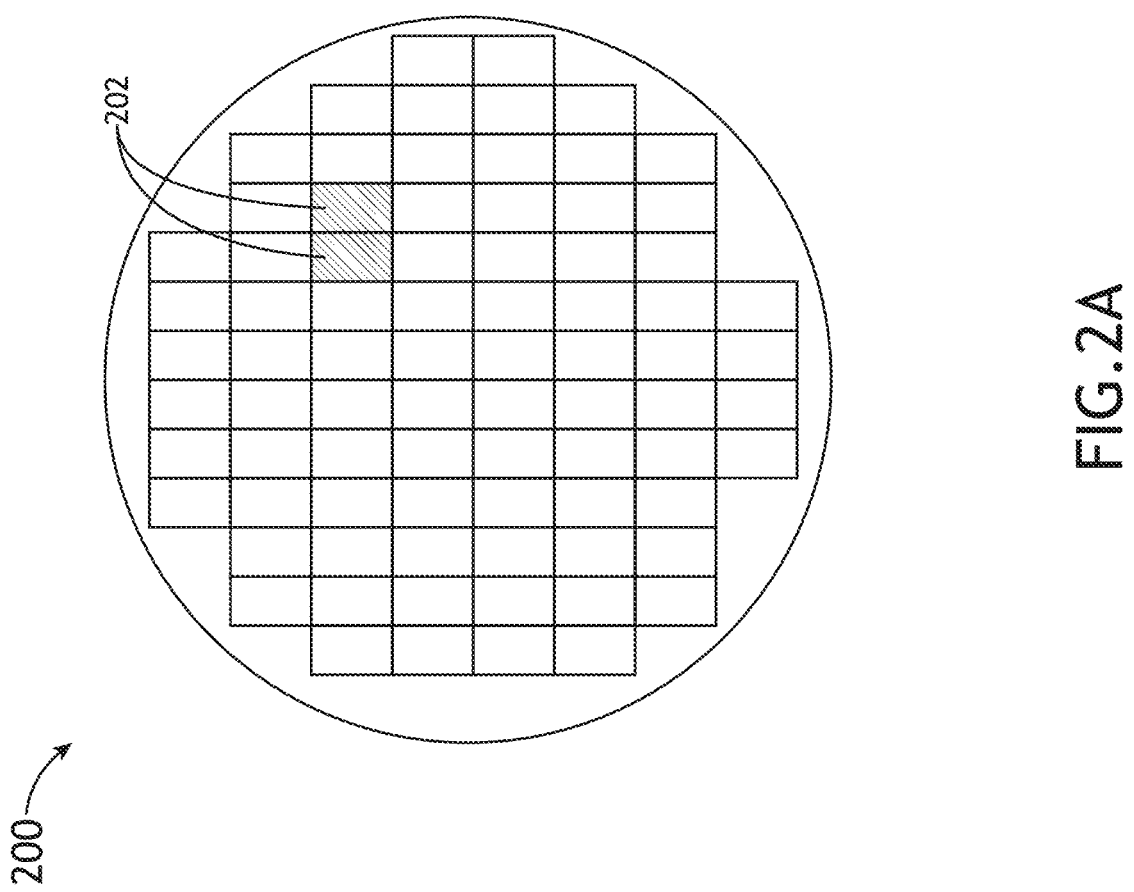
FIG. 2A illustrates a simplified schematic view of a semiconductor wafer map, in accordance with one or more embodiments of the present disclosure.
Figure 2C:
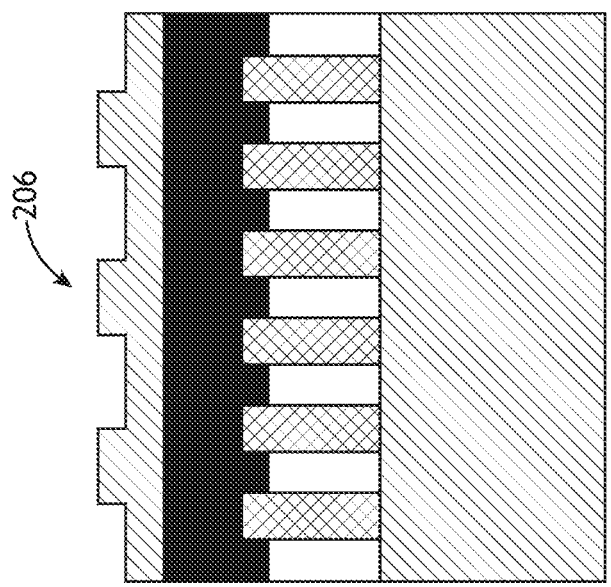
FIG. 2C illustrates a simplified schematic view of a stack design under a semiconductor wafer map pixel representing part of a semiconductor wafer die, in accordance with one or more embodiments of the present disclosure.
Figure 2B:
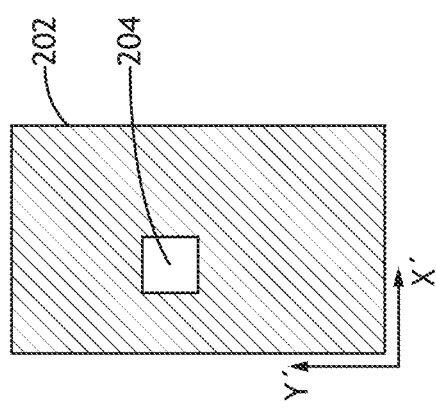
FIG. 2B illustrates a simplified schematic view of semiconductor wafer dies, in accordance with one or more embodiments of the present disclosure.
Figure 2B:
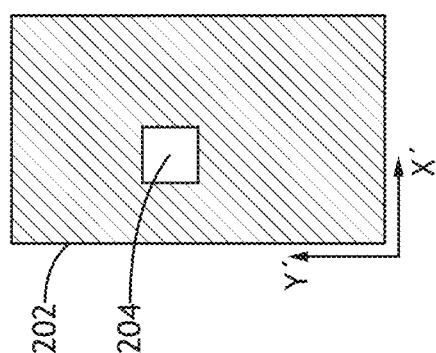

FIGS. 2A-2C generally illustrate a simplified schematic view of semiconductor wafer map 200, in accordance with one or more embodiments of the present disclosure. In one embodiment, the semiconductor wafer map is a pattern wafer geometry (PWG)-based map. For example, the PWG-based map may include, but is not limited to, a topography map. For instance, the topography map may include a full wafer topography map. In this example, the filtering being applied may include, but is not limited to, algorithms to derive nano-topography peak-valley metrics from the topography map.

In another embodiment, the semiconductor wafer map is received from a characterization tool. For example, the characterization tool may include, but is not limited to, a pattern wafer geometry (PWG) tool. It is noted herein, however, that the semiconductor wafer map may be received from an intermediate source (e.g., a server, a controller, or the like), where the intermediate source is communicatively coupled to the characterization tool. In addition, it is noted herein that the semiconductor wafer map may be generated from information received from the characterization tool.

In a step 104, the filtered semiconductor wafer map is separated into one or more dies. In one embodiment, as illustrated in FIGS. 2A-2C, the semiconductor wafer includes one or more dies 202. In another embodiment, a particular die 202 is represented in the semiconductor wafer map 200 by one or more pattern wafer geometry (PWG) dies 202 including one or more pixels 204. In another embodiment, the particular die 202 includes a nominal three-dimensional die stack 206 underneath or below the particular die 202.

In another embodiment, the semiconductor wafer map 200 is separated (e.g., cut) into the one or more die stacks 206 based on one or more select spatial characteristics of the one or more dies 202. For example, the one or more select spatial characteristics may be based on a die size and may include, but are not limited to, width, height, offset, or the like. In another embodiment, the one or more select spatial characteristics are included within the recipe for the semiconductor wafer. In another embodiment, separating the semiconductor wafer map 200 into the one or more die stacks 206 is accomplished via a re-mapping scheme. For example, the re-mapping scheme may be the same re-mapping scheme as the re-mapping scheme implemented in step 102. It is noted herein, however, that the re-mapping scheme may be a different re-mapping scheme from the re-mapping scheme implemented in step 102. Therefore, the above description should not be interpreted as a limitation on the scope of the present disclosure, but merely an illustration.

In a step 106, one or more die comparison statistics are determined for the separated dies. In one embodiment, the determining the die comparison statistics may include subtracting proximate dies 202 from one another to generate comparison data for the dies 202. In another embodiment, the proximate dies 202 are defined by the recipe for the semiconductor wafer. For example, the proximate dies 202 may include a die stack that conforms to approximately nominal arrangements (e.g., similar to the die stack 206). It is noted herein that proximate may refer to "neighboring", "adjacent", or the like.

FIG. 3A-3E generally illustrates comparing data between the one or more dies 202 defined within the semiconductor wafer map 200, in accordance with one or more embodiments of the present disclosure.

In one embodiment, the one or more dies 202 include a center die 300. In another embodiment, the center die 300 is compared to one or more proximate dies 202. For example, the one or more proximate dies 202 may include, but are not limited to, a top die 302, a right die 304, a bottom die 306, and/or a left die 308.

Figure 3B:
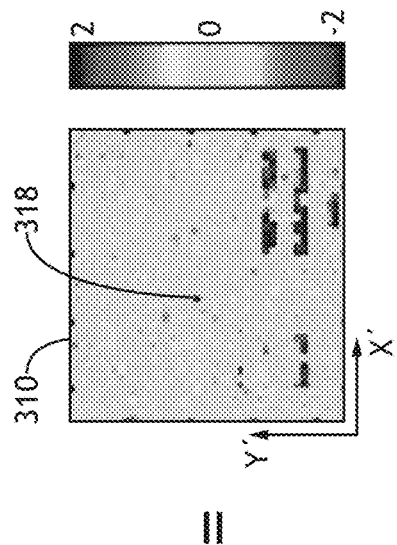
FIG. 3B graphically illustrates data of a comparison between semiconductor wafer dies defined within a semiconductor wafer map, in accordance with one or more embodiments of the present disclosure.
Figure 3B:
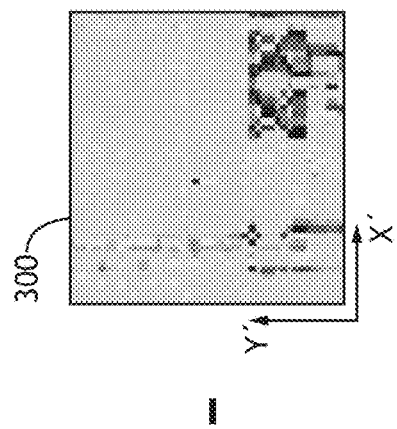
Figure 3B:
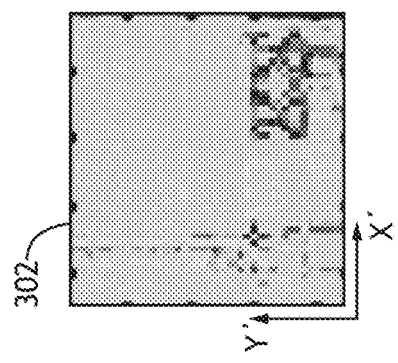
Figure 3C:
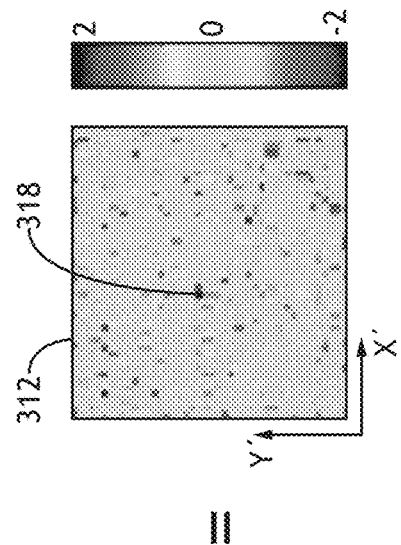
FIG. 3C graphically illustrates data of a comparison between semiconductor wafer dies defined within a semiconductor wafer map, in accordance with one or more embodiments of the present disclosure.
Figure 3C:
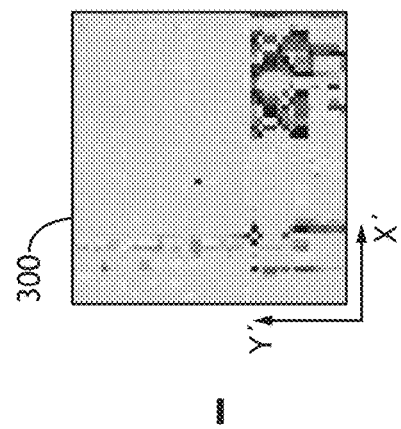
Figure 3C:
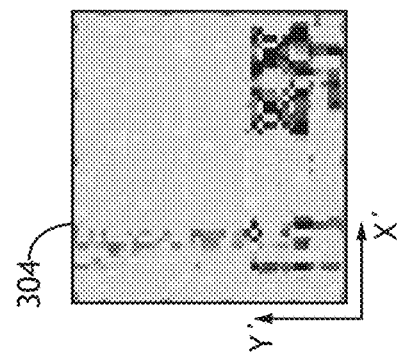
Figure 3D:
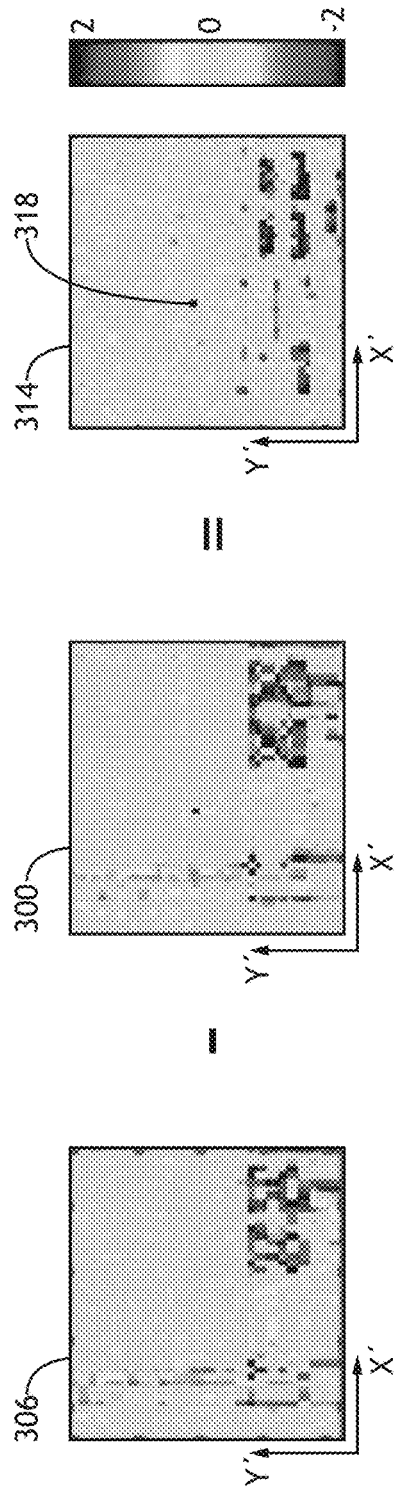
FIG. 3D graphically illustrates data of a comparison between semiconductor wafer dies defined within a semiconductor wafer map, in accordance with one or more embodiments of the present disclosure.
Figure 3E:
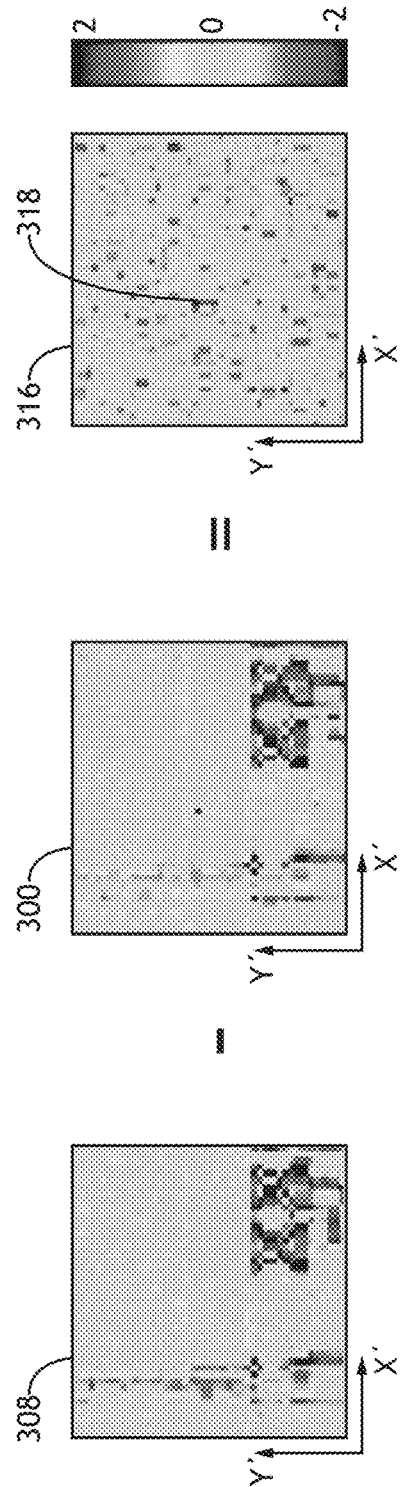
FIG. 3E graphically illustrates data of a comparison between semiconductor wafer dies defined within a semiconductor wafer map, in accordance with one or more embodiments of the present disclosure.

In another embodiment, comparison data is generated by comparing (e.g., subtracting) proximate die 202 data from center die 300 data. For example, where there are four proximate dies 202 (e.g., the top die 302, the right die 304, the bottom die 306, and the left die 308), four sets of comparison data may be generated. For instance, as illustrated in FIG. 3B, top die 302 data may be subtracted from the center die 300 data to generate top-center die 310 data. In addition, as illustrated in FIG. 3C, right die 304 data may be subtracted from the center die 300 data to generate right-center die 312 data. Further, as illustrated in FIG. 3D, bottom die 306 data may be subtracted from the center die 300 data to generate bottom-center die 314 data. Further, as illustrated in FIG. 3E, left die 308 data may be subtracted from the center die 300 data to generate left-center die 316 data.

In another embodiment, one or more sets of comparison data (e.g., top-center die 310 data, right-center die 312 data, bottom-center die 314 data, and the left-center die 316 data) generated by comparing the center die 300 data to proximate die 202 data includes one or more excursions 318 within the center die 300.

Although the present disclosure is directed to comparing data for a particular center die 300 to data of four proximate dies 202 (e.g., as illustrated in FIGS. 3B-3E), it is noted herein that data for a particular center die 300 may only need to be compared to data of two proximate dies 202 to ensure that a possible excursion 318 is pinpointed to the particular center die 300 under review. For example, the excursion 318 being present in the comparison data generated by comparing the particular center die 300 data and the data of both of the two proximate dies 202 would pinpoint the possible excursion 318 to the particular center die 300 under review.

In another embodiment, the comparative process shifts to review a new center die 300. For example, the comparative process may shift to the right in FIG. 3A, such that the former right die 304 becomes a new center die 300, the former center die 300 becomes a new left die 308, and one or more of a new top die, a new right die, and a new bottom die are utilized for purposes of comparison. In this regard, every die 202 on the semiconductor wafer may be checked for excursions 318.

Although embodiments of the present disclosure are directed to comparing between proximate dies 202 on the same semiconductor wafer, it is noted herein that dies 202 having the same common structure may be compared across multiple semiconductor wafers. Therefore, the above description should not be interpreted as a limitation on the scope of the present disclosure, but merely an illustration.

Although the present disclosure is directed to comparison between proximate dies 202 on the same semiconductor wafer, it is noted herein that the comparison may be made between a particular die 202 and a "golden die" (or "golden reference die"). For example, the golden die may be generated via a first scan of a particular die 202 on the same wafer, which may be then compared to subsequent scans of the same die on the same wafer. By way of another example, the golden die scan and the subsequent die scans may be obtained from different wafers. By way of another example, the golden die may be a version of a particular die known to be correct (e.g., by a manufacturer), which may then be compared to scans of the same die on different wafers. Therefore, the above description should not be interpreted as a limitation on the scope of the present disclosure, but merely an illustration.

In another embodiment, the statistics of the die comparison are generated from the comparison data. In another embodiment, statistics are generated for the pixels 204 within the proximate dies 202, where the proximate dies 202 include a common structure. For example, the statistics for the pixels 204 within the proximate dies 202 may be determined on a per-pixel basis. For instance, a die 202 with 1000 pixels 204 may be repeated 50 times across the semiconductor wafer map 200, meaning the semiconductor wafer map 200 may include 50 instances of the common structures for each of the 1000 pixels 204.

Although the present disclosure is directed to comparing proximate dies 202, it is noted herein that the description provided may be narrowed to comparing proximate pixels 204. Therefore, the above description should not be interpreted as a limitation on the scope of the present disclosure, but merely an illustration.

In a step 108, an inspection threshold is established based on the generated die comparison statistics. In one embodiment, one or more data analysis algorithms are applied to the die comparison statistics generated from the comparison data to establish the inspection threshold. For example, a histogram may be generated from the die comparison statistics to establish the inspection threshold. For instance, the inspection threshold may be a three-sigma deviation within the histogram. It is noted herein the established inspection threshold may include a positive value or a negative value.

In another embodiment, the established inspection threshold is selected for a single region of interest for a particular die 202. It is noted herein, however, that the established inspection threshold may be segmented into multiple, different regions of interest for the particular die 202. In another embodiment, the established inspection threshold may be of a select spatial extent. For example, the established inspection threshold may range from a single threshold per die that encompasses all pixels within the particular die 202 to an individual threshold for each pixel within the particular die 202.

In a step 110, one or more excursion maps are generated based on the established inspection threshold. In one embodiment, the established inspection threshold is applied to the generated die comparison statistics of the generated comparison data. For example, any value exceeding the established inspection threshold (e.g., the value is greater than a positive threshold or is less than a negative threshold) in the die comparison statistics for at least two of the comparison data corresponding to a particular center die 300 is treated as an excursion (e.g., geometry deviation) within the particular center die 300 as compared to the proximate dies 202 of the particular center die 300, instead of being considered random noise in the particular center die 300. It is noted herein that the established inspection threshold is applied to the die comparison statistics for the comparison data instead of the original die 202 data to account for drift between a first die-to-die inspection process and a subsequent die-to-die inspection process. It is noted, however, that the established inspection threshold may be applied to the original die 202 data. In another embodiment, one or more final region and/or pixel-based inspection maps are generated from the application of the established inspection threshold to the generated die comparison statistics. In another embodiment, the one or more final region and/or pixel-based inspection maps are combined (e.g., consolidated or blobbed) into the one or more excursion maps.

Although embodiments of the present disclosure are directed to determining the one or more excursion maps based on the established inspection threshold, it is noted herein that the one or more excursion maps may be based on a user-specified inspection threshold. For example, the description provided with respect to the using of the established inspection threshold in at least step 110 of the method 100 may be directed to the user-specified inspection threshold. For instance, the user-specified inspection threshold may at least be applied to the generated die comparison statistics instead of the established inspection threshold being applied to the generated die comparison statistics. Therefore, the above description should not be interpreted as a limitation on the scope of the present disclosure, but merely an illustration.

In a step 112, excursions are detected within the excursion maps. In one embodiment, one or more additional post-processing processes are applied to select pixels that indicate a possible location of an excursion within the one or more excursion maps to detect the excursions.

It is noted herein that combining pattern wafer geometry metrology processes with wafer inspection processes may expand excursion detection beyond the conventional die statistics-based issue reporting mechanism to which metrology characterization tools are traditionally limited, thus improving the performance of metrology characterization tool processes. Notably, the combination of pattern wafer geometry metrology processes (e.g., full wafer topography mapping) with wafer inspection processes (e.g., die-to-die inspection) may expand the capability of surface geometry characterization tools to cover surface geometry excursion monitoring. In addition, the combination may assist in penetration during pattern wafer geometry (PWG) characterization and fabrication of integrated circuitry (IC). For example, the combination may enable a pattern wafer geometry (PWG) product line to check for a product wafer high volume manufacturing (HVM) excursion monitoring without a limitation of an opaque top coating, while including an insensitivity to transparent film error. In this regard, the combination may be used with any pattern wafer transparent film stack with a transparent film error limitation (which, it is noted herein, is generally believed not possible for optical surface metrology alone).

Figure 4:
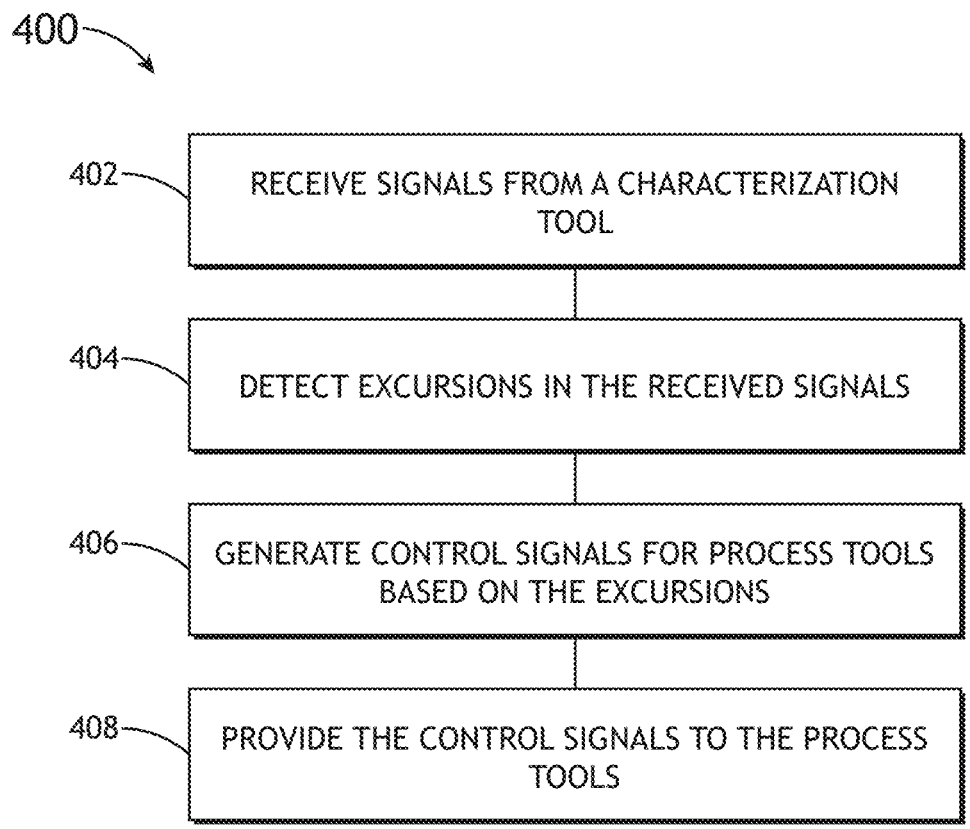
FIG. 4 illustrates a flow diagram of a method for process-induced excursion characterization during semiconductor device production, in accordance with one or more embodiments of the present disclosure.

Although embodiments of the present disclosure are directed to determining the one or more excursion maps for purposes of excursion monitoring, it is noted herein that the one or more excursion maps may be generated to be utilized during the research and development of semiconductor production processes. FIG. 4 illustrates a flow diagram of a method 400 for process-induced excursion characterization during semiconductor device production, in accordance with one or more embodiments of the present disclosure.

In a step 402, one or more signals are received from a characterization tool. In one embodiment, the one or more signals are generated by the characterization tool in response to a scanning of a semiconductor wafer. In another embodiment, the characterization tool includes a PWG-based characterization tool.

In a step 404, semiconductor wafer excursions are detected in the received signals. In one embodiment, the one or more excursions are detected via one or more steps of the method 100.

In a step 406, one or more control signals are generated for one or more process tools based on the detected excursions. In one embodiment, the one or more control signals improve performance of a semiconductor fabrication process by adjusting a corresponding process tool (e.g., semiconductor device process tool) responsible for an excursion observed within the one or more generated excursion maps.

In a step 408, the one or more control signals are provided to the one or more process tools. In one embodiment, the one or more control signals may be provided to a process tool via a feedback loop (e.g., to a process tool positioned within the fabrication process line before the characterization tool) to prevent the excursion on subsequent wafers. In another embodiment, the one or more control signals may be provided to a process tool via a feed-forward loop (e.g., to a process tool positioned within the fabrication process line after the characterization tool) to compensate for the excursion on the same semiconductor wafer.

It is noted herein the method 100 and/or the method 400 is not limited to the steps provided. For example, the method 100 and/or the method 400 may instead include more or fewer steps. By way of another example, the method 100 and/or the method 400 may perform the steps in an order other than provided. Therefore, the above description should not be interpreted as a limitation on the scope of the present disclosure, but merely an illustration.

Figure 5:
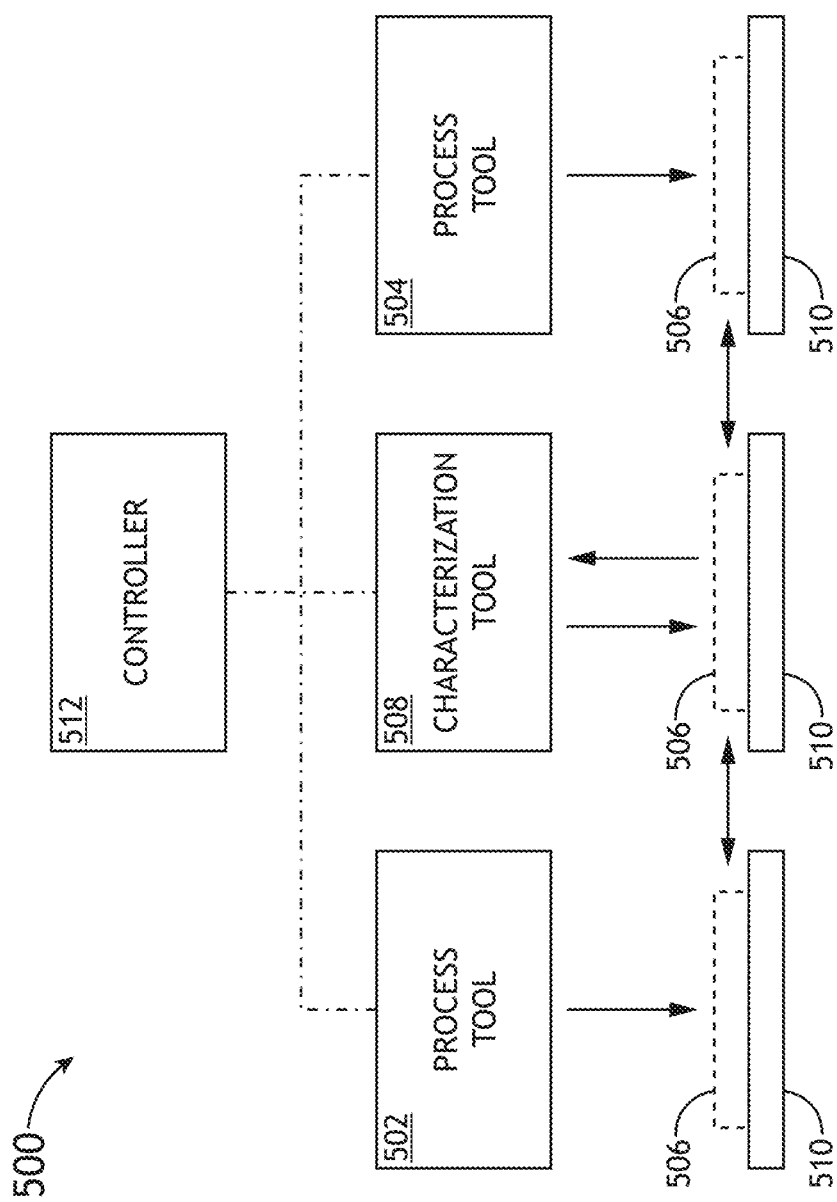
FIG. 5 illustrates a simplified block diagram of a system for process-induced excursion characterization during semiconductor device production, in accordance with one or more embodiments of the present disclosure.
Figure 6:
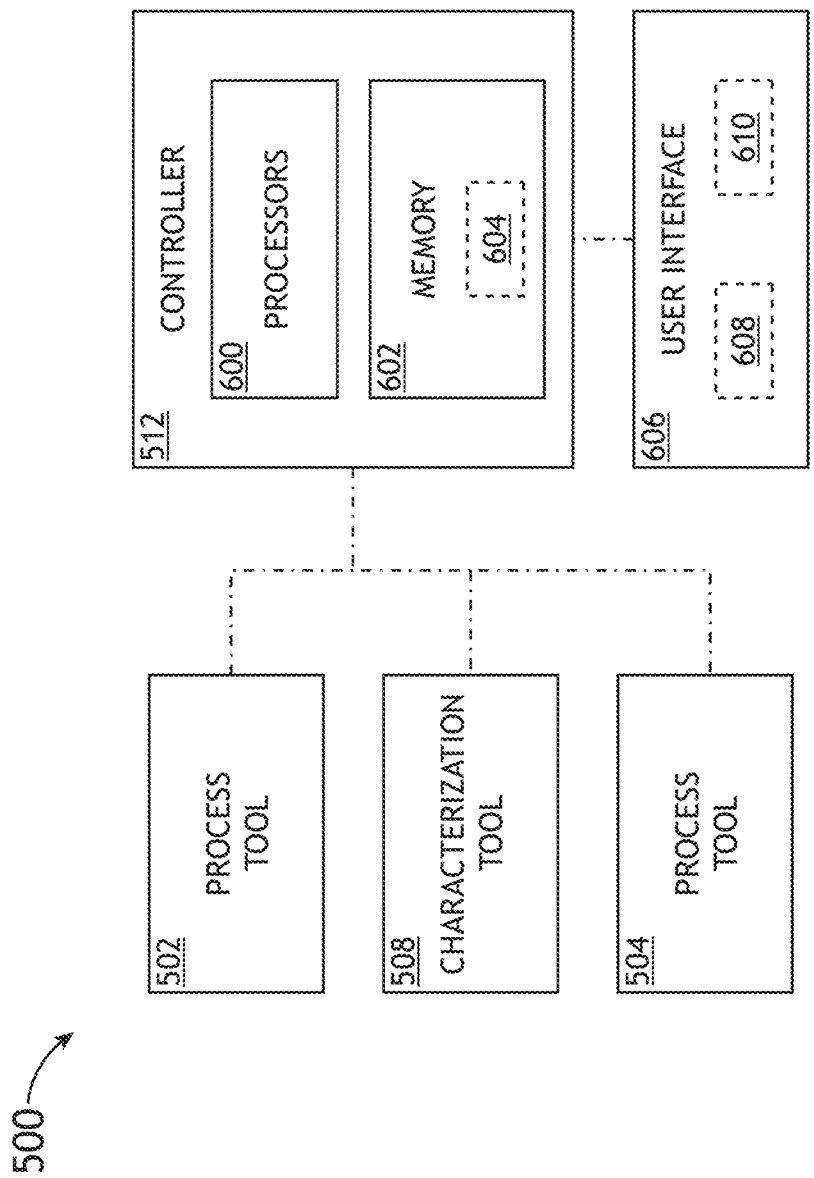
FIG. 6 illustrates a simplified block diagram of a system for process-induced excursion characterization during semiconductor device production, in accordance with one or more embodiments of the present disclosure.

FIGS. 5 and 6 generally illustrate a system 500 for process-induced excursion characterization during semiconductor device production, in accordance with one or more embodiments of the present disclosure.

In one embodiment, the system 500 is configured to perform one or more semiconductor production processes.

In another embodiment, the one or more semiconductor production processes include one or more semiconductor fabrication processes. For example, the one or more semiconductor fabrication processes may include, but are not limited to, one or more lithographic processes such as substrate preparation, spin coating, pre-bake processes, exposure processes, post-exposure baking processes, development processes, post-bake processes, or the like. For instance, the one or more lithographic processes may include, but are not limited to, patterning processes, etching processes, stripping processes, annealing processes, chemical mechanical planarization (CMP) processes, or the like. By way of another example, the one or more semiconductor fabrication processes may include, but are not limited to, one or more film deposition processes. For example, the one or more film deposition processes may include, but are not limited to, chemical vapor deposition (CVD) processes, physical vapor deposition (PVD) processes, or the like. In another embodiment, the system 500 includes one or more process tools 502 and/or one or more process tools 504 configured to perform the one or more semiconductor fabrication processes.

For example, the one or more process tools 502 and/or the one or more process tools 504 may include one or more lithography process tools. For instance, the one or more lithography process tools may include, but are not limited to, patterning tools, etching tools, semiconductor doping tools, or the like. Generally, the one or more lithography process tools may include any lithography process tool known in the art. Therefore, the above description should not be interpreted as a limitation on the scope of the present disclosure, but merely an illustration.

By way of another example, the one or more process tools 502 and/or the one or more process tools 504 may include one or more film deposition tools. For instance, the one or more film deposition tools may deposit one or more films to form one or more layers on a sample 506. A layer may include one or more films fabricated by a set of semiconductor production processes that begins with the patterning of an intended design and ends immediately before the patterning of the next design for the next layer. The one or more films may be deposited based on an operating recipe. For example, the one or more films may be deposited on a front side of the sample 506 (e.g., frontside film), a back side of the sample 506 (e.g., a backside film), and/or on a layer previously deposited on the sample 506.

In another embodiment, the sample 506 includes any sample suitable for characterization (e.g., review, imaging overlay, or the like). For example, the sample 506 may include, but is not limited to, a photomask/reticle, semiconductor wafer, or the like. As used through the present disclosure, the term "wafer" refers to a substrate formed of a semiconductor and/or a non-semiconductor material. For instance, in the case of a semiconductor material, the wafer may be formed from, but is not limited to, monocrystalline silicon, gallium arsenide, and/or indium phosphide. As such, the term "wafer" and the term "sample" may be used interchangeably in the present disclosure. Therefore, the above description should not be interpreted as a limitation on the scope of the present disclosure but merely an illustration.

It is noted herein that many different types of devices may be formed on a wafer, and the term wafer as used herein is intended to encompass a wafer on which any type of device known in the art is being fabricated. Therefore, the above description should not be interpreted as a limitation on the scope of the present disclosure but merely an illustration.

In another embodiment, the one or more semiconductor production processes include one or more semiconductor characterization processes. For example, the one or more semiconductor characterization processes may be performed before, between, and/or following the one or more semiconductor production processes. By way of another example, the one or more semiconductor characterization processes may include one or more metrology processes. For instance, the one or more metrology processes may include, but are not limited to, full wafer topography metrology and/or pattern wafer geometry (PWG) metrology. It is noted herein the one or more metrology processes may include determining statistical values for select die metrics on the wafer and comparing the statistics of the select dies, as opposed to inspection processes (e.g., die-to-die inspection) which may include focusing on non-repeat defects between neighboring dies via generated optical signals or electron-beam signals.

In another embodiment, the system 500 includes one or more characterization tools 508 configured to perform the one or more semiconductor characterization processes. For example, the one or more characterization tools 508 may include, but are not limited to, one or more metrology tools. By way of another example, the one or more characterization tools 508 may include, but are not limited to, one or more inspection tools. Generally, the one or more characterization tools 508 may include any review tool, imaging-based overlay metrology tool, inspection tool, or similar tool known in the art suitable for inspecting one or more wafers, reticles, or photomasks.

For example, the one or more characterization tools 508 may include, but are not limited to, one or more wafer geometry (WG) tools or pattern wafer geometry (PWG) tools (e.g., an interferometer) configured to measure one or more spatial characteristics of the sample 506. For instance, the one or more spatial characteristics may include, but are not limited to, height (e.g., frontside height or backside height), thickness variation, flatness, and derivatives such as shape, shape-difference, nano-topography, or the like. It is noted herein the one or more spatial characteristics of the sample 506 may be related to the wafer geometry of the sample 506. In addition, it is noted herein that the characterization tools 508 may be adapted to characterize pattern wafer geometry on the sample 506, where the dynamic range of the sample 506 slope (e.g., wafer slope) measured by the PWG-based characterization tools is extended by stitching measurement results of different regions of the sample 506 together. Therefore, the above description should not be interpreted as a limitation on the scope of the present disclosure, but merely an illustration.

By way of another example, the one or more characterization tools 508 may include one or more inspection tools. For instance, the one or more inspection tools may include an optical characterization tool capable of generating one or more high-resolution images representing the electrical intent of the sample 506 and capable of operating at a wavelength corresponding to, but not limited to, visible light, UV radiation, DUV radiation, VUV radiation, EUV radiation, and/or X-ray radiation. In addition, the one or more inspection tools may include a broadband inspection tool including, but not limited to, a laser sustained plasma (LSP) based inspection tool. Further, the one or more inspection tools may include a narrowband characterization tool, such as, but not limited to, a laser scanning inspection tool.

In another embodiment, the sample 506 is transferred between the one or more process tools 502, the one or more process tools 504, and/or the one or more characterization tools 508 during the semiconductor production process. For example, the one or more characterization tools 508 may perform the one or more semiconductor characterization processes before, between, and/or after the one or more semiconductor fabrication processes.

In another embodiment, the determined excursions in the one or more semiconductor fabrication processes may be prevented in subsequent fabrication processes on subsequent samples 506 (e.g., in a feedback loop). For example, the one or more process tools 502 may be adjustable in a feedback loop based on the determined excursions in the one or more semiconductor fabrication processes. In another embodiment, the determined excursions in the one or more semiconductor fabrication processes may be compensated for in subsequent fabrication processes on the same sample 506 (e.g., in a feed forward loop). For example, the one or more process tools 504 may be adjustable in the feed forward loop based on the determined excursions in the one or more semiconductor fabrication processes.

In another embodiment, the sample 506 is secured via a sample stage 510 proximate to the process tools 502, the one or more process tools 504, and/or the one or more characterization tools 508. For example, the one or more process tools 502, the one or more process tools 504, and/or the one or more characterization tools 508 may each have a separate sample stage 510. By way of another example, at least some of the one or more process tools 502, the one or more process tools 504, and/or the one or more characterization tools 508 may share a common sample stage 510.

The sample stage 510 may include any appropriate mechanical and/or robotic assembly known in the art of semiconductor characterization. For example, the sample stage 510 may be configured to secure the sample 506 via contact with at least a portion of a frontside surface and/or a backside surface of the sample 506. For instance, the sample stage 510 may include, but is not limited to, a platform. By way of another example, the sample stage 510 may be configured to secure the sample 506 via contact with a thickness surface and/or an edge of the sample 506. For instance, the sample stage 510 may include, but is not limited to, one or more point contact devices.

The sample stage 510 may include an actuatable stage. For example, the sample stage 510 may include, but is not limited to, one or more translational stages suitable for selectively translating the sample 506 along one or more linear directions (e.g., x-direction, y-direction, and/or z-direction). By way of another example, the sample stage 510 may include, but is not limited to, one or more rotational stages suitable for selectively rotating the sample 506 along a rotational direction. By way of another example, the sample stage 510 may include, but is not limited to, one or more translational and rotational stages suitable for selectively translating the sample 506 along a linear direction and/or rotating the sample 506 along a rotational direction. By way of another example, the sample stage 510 may be configured to translate or rotate the sample 506 for positioning, focusing, and/or scanning in accordance with a selected characterization process (e.g., review, imaging overlay, inspection, or the like), several of which are known to the art.

In one embodiment, the system 500 includes a controller 512. For example, the controller 512 may be communicatively coupled to the one or more process tools 502, the one or more process tools 504, and/or the one or more characterization tools 508 by a transmission medium that may include wireline and/or wireless portions.

In another embodiment, the controller 512 includes one or more processors 600 and/or memory 602. In another embodiment, the memory 602 stores one or more set of program instructions 604. In another embodiment, a user interface 606 is communicatively coupled to and/or integrated with the controller 512. For example, the controller 512 may be coupled to the user interface 606 via a transmission medium that may include wireline and/or wireless portions. In another embodiment, the user interface 606 includes one or more display devices 608 and/or one or more user input devices 610. In another embodiment, the one or more display devices 608 are coupled to the one or more user input devices 610. For example, the one or more display devices 608 may be coupled to the one or more user input devices 610 by a transmission medium that may include wireline and/or wireless portions.

The controller 512 may be configured to receive and/or acquire data or information from other systems or subsystems (e.g., the one or more process tools 502, the one or more process tools 504, the one or more characterization tools 508, the user interface 606, or the like) of the system 500 via a transmission medium that may include wireline and/or wireless portions. The controller 512 may in addition be configured to transmit data or information (e.g., the output of one or more procedures of the inventive concepts disclosed herein) to one or more systems or sub-systems (e.g., the one or more process tools 502, the one or more process tools 504, the one or more characterization tools 508, the user interface 606, or the like) of the system 500 by a transmission medium that may include wireline and/or wireless portions. In this regard, the transmission medium may serve as a data link between the controller 512 and the other subsystems of the system 500. In addition, the controller 512 may be configured to send data to external systems via a transmission medium (e.g., network connection).

The one or more processors 600 may include any one or more processing elements known in the art. In this sense, the one or more processors 600 may include any microprocessor device configured to execute algorithms and/or program instructions 604. For example, the one or more processors 600 may consist of a desktop computer, mainframe computer system, workstation, image computer, parallel processor, handheld computer (e.g., tablet, smartphone, or phablet), or another computer system (e.g., networked computer). In general, the term "processor" may be broadly defined to encompass any device having one or more processing elements, which execute the one or more sets of program instructions 604 from a non-transitory memory medium (e.g., the memory 602). Moreover, different subsystems of the system 500 (e.g., the one or more process tools 502, the one or more process tools 504, the one or more characterization tools 508, the user interface 606, or the like) may include processor or logic elements suitable for carrying out at least a portion of the steps described throughout the present disclosure. Therefore, the above description should not be interpreted as a limitation on the present disclosure but merely an illustration.

The memory 602 may include any storage medium known in the art suitable for storing the one or more sets of program instructions 604 executable by the associated one or more processors 600. For example, the memory 602 may include a non-transitory memory medium. For instance, the memory 602 may include, but is not limited to, a read-only memory, a random-access memory, a magnetic or optical memory device (e.g., disk), a magnetic tape, a solid-state drive, and the like. The memory 602 may be configured to provide display information to a display device of the user interface 606. The memory 602 may in addition be configured to store user input information from a user input device of the user interface 606. The memory 602 may be housed in a common controller 512 housing with the one or more processors 600. The memory 602 may, alternatively or in addition, be located remotely with respect to the spatial location of the processors 600 and/or the controller 512. For instance, the one or more processors 600 and/or the controller 512 may access a remote memory 602 (e.g., server), accessible through a network (e.g., internet, intranet, and the like).

In another embodiment, the controller 512 executes one or more semiconductor fabrication processes, one or more semiconductor characterization processes, one or more modelling processes, and/or one or more system analysis processes from program instructions 604 stored on memory 602 via the one or more processors 600. For example, the one or more program instructions 604 may be configured to cause the one or more processors 600 to apply filtering to a semiconductor wafer map, separate the filtered semiconductor wafer map into die stacks, generate die comparison statistics by comparing proximate die stacks, and/or generate excursion maps by applying at least one inspection threshold to the die comparison statistics. By way of another example, the one or more program instructions 604 may be configured to cause the one or more processors 600 to receive signals from a characterization tool and/or generate control signals based on the determined excursion maps for process tools. Generally, the one or more sets of program instructions 604 may be configured to cause the one or more processors 600 to carry out any steps of the one or more methods (e.g., the method 100 and/or the method 400) described throughout the present disclosure.

Although embodiments of the present disclosure illustrate the controller 512 as a stand-alone component from the one or more process tools 502, the one or more process tools 504, and/or from the one or more characterization tools 508, it is noted herein that any fabrication processes, characterization processes, modelling processes, and/or system analysis processes for determining spatial characteristics of the sample 506 may be implemented via a controller integrated within the one or more process tools 502, the one or more process tools 504, and/or within the one or more characterization tools 508. Therefore, the above description should not be interpreted as a limitation on the scope of the present disclosure but merely an illustration.

The one or more display devices 608 may include any display device known in the art. For example, the one or more display devices 608 may include, but is not limited to, a liquid crystal display (LCD). By way of another example, the one or more display devices 608 may include, but is not limited to, an organic light-emitting diode (OLED) based display. By way of another example, the one or more display devices 608 may include, but is not limited to a CRT display. Those skilled in the art should recognize that a variety of display devices may be suitable for implementation in the present invention and the particular choice of display device may depend on a variety of factors, including, but not limited to, form factor, cost, and the like. Generally, any display device capable of integration with a user input device (e.g., touchscreen, bezel mounted interface, keyboard, mouse, trackpad, and the like) is suitable for implementation in the present invention.

The one or more user input devices 610 may include any user input device known in the art. For example, the one or more user input devices 610 may include, but is not limited to, a keyboard, a keypad, a touchscreen, a lever, a knob, a scroll wheel, a track ball, a switch, a dial, a sliding bar, a scroll bar, a slide, a handle, a touch pad, a paddle, a steering wheel, a joystick, a bezel input device, or the like. In the case of a touchscreen interface, those skilled in the art should recognize that a large number of touchscreen interfaces may be suitable for implementation in the present invention. For instance, the one or more display devices 608 may be integrated with a touchscreen interface, such as, but not limited to, a capacitive touchscreen, a resistive touchscreen, a surface acoustic based touchscreen, an infrared based touchscreen, or the like. Generally, any touchscreen interface capable of integration with the display portion of a display device is suitable for implementation in the present invention. In another embodiment, the one or more user input devices 610 may include, but is not limited to, a bezel mounted interface.

Although embodiments of the present disclosure describe the one or more process tools 502, the one or more process tools 504, and the one or more characterization tools 508 as components of the system 500, it is noted herein that the one or more process tools 502, the one or more process tools 504, and/or the one or more characterization tools 508 may not be integral or required components of the system 500. For example, the one or more process tools 502, the one or more process tools 504, and/or the one or more characterization tools 508 may be components separate from and communicatively coupled to the system 500 via an intermediate source (e.g., the controller 512, a server, or the like). Therefore, the above description should not be interpreted as a limitation on the scope of the present disclosure but merely an illustration.

Although embodiments of the present disclosure describe the controller 512 as a component of the system 500, it is noted herein that the controller 512 may not be an integral or required component of the system 500. In addition, while embodiments of the present disclosure describe the user interface 606 as a component of the system 500, it is noted herein that the user interface 606 may not be an integral or required component of the system 500. Therefore, the above description should not be interpreted as a limitation on the scope of the present disclosure but merely an illustration.

Advantages of the present disclosure include process-induced excursion characterization. Advantages of the present disclosure also include improving the performance of characterization tools via control of characterization processes in response to excursions located by combining wafer geometry metrology processes with wafer inspection processes to promote an increased sensitivity and accuracy when detecting excursions caused by the fabrication processes. Advantages of the present disclosure also include improving the performance of fabrication tools via control of fabrication processes by adjusting the fabrication tools in response to excursions located by combining wafer geometry metrology processes with wafer inspection processes to promote an increased sensitivity and accuracy when detecting excursions caused by the fabrication processes.

Those having skill in the art will recognize that the state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and/or firmware.

In some implementations described herein, logic and similar implementations may include software or other control structures. Electronic circuitry, for example, may have one or more paths of electrical current constructed and arranged to implement various functions as described herein. In some implementations, one or more media may be configured to bear a device-detectable implementation when such media hold or transmit device-detectable instructions operable to perform as described herein. In some variants, for example, implementations may include an update or modification of existing software or firmware, or of gate arrays or programmable hardware, such as by performing a reception of or a transmission of one or more instructions in relation to one or more operations described herein. Alternatively or in addition, in some variants, an implementation may include special-purpose hardware, software, firmware components, and/or general-purpose components executing or otherwise invoking special-purpose components. Specifications or other implementations may be transmitted by one or more instances of tangible transmission media as described herein, optionally by packet transmission or otherwise by passing through distributed media at various times.

Alternatively, or in addition, implementations may include executing a special-purpose instruction sequence or invoking circuitry for enabling, triggering, coordinating, requesting, or otherwise causing one or more occurrences of virtually any functional operations described herein. In some variants, operational or other logical descriptions herein may be expressed as source code and compiled or otherwise invoked as an executable instruction sequence. In some contexts, for example, implementations may be provided, in whole or in part, by source code, such as C++, or other code sequences. In other implementations, source or other code implementation, using commercially available and/or techniques in the art, may be compiled/implemented/translated/converted into a high-level descriptor language (e.g., initially implementing described technologies in C, C++, python, Ruby on Rails, Java, PHP, .NET, or Node.js programming language and thereafter converting the programming language implementation into a logic-synthesizable language implementation, a hardware description language implementation, a hardware design simulation implementation, and/or other such similar mode(s) of expression). For example, some or all of a logical expression (e.g., computer programming language implementation) may be manifested as a Verilog-type hardware description (e.g., via Hardware Description Language (HDL) and/or Very High Speed Integrated Circuit Hardware Descriptor Language (VHDL)) or other circuitry model which may then be used to create a physical implementation having hardware (e.g., an Application Specific Integrated Circuit). Those skilled in the art will recognize how to obtain, configure, and optimize suitable transmission or computational elements, material supplies, actuators, or other structures in light of these teachings.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

Generally, those skilled in the art will recognize that the various embodiments described herein can be implemented, individually and/or collectively, by various types of electro-mechanical systems having a wide range of electrical components such as hardware, software, firmware, and/or virtually any combination thereof; and a wide range of components that may impart mechanical force or motion such as rigid bodies, spring or torsional bodies, hydraulics, electro-magnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Those skilled in the art will also appreciate that examples of electro-mechanical systems include but are not limited to a variety of consumer electronics systems, medical devices, as well as other systems such as motorized transport systems, factory automation systems, security systems, and/or communication/computing systems. Those skilled in the art will recognize that electro-mechanical as used herein is not necessarily limited to a system that has both electrical and mechanical actuation except as context may dictate otherwise.

Generally, those skilled in the art will recognize that the various aspects described herein which can be implemented, individually and/or collectively, by a wide range of hardware, software, firmware, and/or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). Those having skill in the art will recognize that the subject matter described herein may be implemented in an analog or digital fashion or some combination thereof.

Those skilled in the art will recognize that at least a portion of the devices and/or processes described herein can be integrated into a data processing system. Those having skill in the art will recognize that a data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

Although a user is described herein as a single figure, those skilled in the art will appreciate that the user may be representative of a human user, a robotic user (e.g., computational entity), and/or substantially any combination thereof (e.g., a user may be assisted by one or more robotic agents) unless context dictates otherwise. Those skilled in the art will appreciate that, in general, the same may be said of "sender" and/or other entity-oriented terms as such terms are used herein unless context dictates otherwise.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configurable to," "operable/operative to," "adapted/adaptable," "able to," "conformable/conformed to," etc. Those skilled in the art will recognize that such terms (e.g., "configured to") can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

Although particular embodiments of this invention have been illustrated, it is apparent that various modifications and embodiments of the invention may be made by those skilled in the art without departing from the scope and spirit of the foregoing disclosure. It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes. Accordingly, the scope of the invention should be limited only by the claims appended hereto.

What is claimed:

1. A system, comprising:
    a controller, wherein the controller includes one or more processors and memory configured to store one or more sets of program instructions, wherein the one or more processors are configured to execute the one or more sets of program instructions, wherein the one or more sets of program instructions are configured to cause the one or more processors to:
        apply filtering to a semiconductor wafer map;
        separate the filtered semiconductor wafer map into a plurality of dies;
        generate a set of die comparison statistics for the plurality of dies;
        generate at least one excursion map by applying at least one inspection threshold to the set of die comparison statistics; and
        detect at least one excursion within the at least one excursion map.

2. The system in claim 1, wherein the semiconductor wafer map is received from a characterization tool.

3. The system in claim 1, wherein the semiconductor wafer map includes a pattern wafer geometry-based map.

4. The system in claim 3, wherein the pattern wafer geometry-based map includes a full wafer topography map.

5. The system in claim 1, wherein the one or more sets of program instructions are configured to cause the one or more processors to separate the filtered semiconductor wafer map into the plurality of dies based on one or more select spatial characteristics of the plurality of dies.

6. The system in claim 1, wherein the generating the set of die comparison statistics includes comparing a set of dies of the plurality of dies.

7. The system in claim 6, wherein the set of dies of the plurality of dies includes a center die and one or more proximate dies.

8. The system in claim 7, wherein the one or more proximate dies are adjacent to the center die.

9. The system in claim 7, wherein the comparing the set of dies of the plurality of dies includes generating comparison data by subtracting data corresponding to the one or more proximate dies from data corresponding to the center die.

10. The system in claim 9, wherein the comparing the set of dies of the plurality of dies includes generating comparison data by subtracting data corresponding to at least two proximate dies from data corresponding to the center die.

11. The system in claim 9, wherein the set of die comparison statistics is determined from the generated comparison data.

12. The system in claim 11, wherein the set of die comparison statistics are generated for a plurality of pixels within the set of dies of the plurality of dies.

13. The system in claim 12, wherein the set of die comparison statistics are determined on a per-pixel basis for the plurality of pixels within the set of dies of the plurality of dies.

14. The system in claim 11, wherein the at least one inspection threshold is established based on the set of die comparison statistics.

15. The system in claim 14, wherein establishing the at least one inspection threshold based on the generated set of die comparison statistics includes applying one or more data analysis algorithms to the generated set of die comparison statistics.

16. The system in claim 15, wherein the at least one excursion is detected when a value of the generated comparison data exceeds the established at least one inspection threshold.

17. The system in claim 11, wherein the at least one inspection threshold is user-specified.

18. The system in claim 1, wherein the one or more sets of program instructions are further configured to cause the one or more processors to:
    provide one or more control signals to at least one process tool to improve performance of one or more fabrication processes, wherein the one or more control signals are generated based on the at least one excursion.

19. The system in claim 18, wherein the improving the performance of one or more fabrication processes includes adjusting the at least one process tool to reduce one or more excursions caused by the one or more fabrication processes.

20. The system in claim 18, wherein the one or more control signals are provided to the at least one process tool via at least one of a feed forward loop or a feedback loop.

21. A system, comprising:
    a characterization tool; and
    a controller, wherein the controller includes one or more processors and memory configured to store one or more sets of program instructions, wherein the one or more processors are configured to execute the one or more sets of program instructions, wherein the one or more sets of program instructions are configured to cause the one or more processors to:

apply filtering to a semiconductor wafer map from the characterization tool;

separate the filtered semiconductor wafer map into a plurality of dies;

generate a set of die comparison statistics for the plurality of dies;

generate at least one excursion map by applying at least one inspection threshold to the set of die comparison statistics; and detect at least one excursion within the at least one excursion map.

22. The system in claim 21, wherein the at least one inspection threshold is established based on the set of die comparison statistics.

23. The system in claim 21, wherein the at least one inspection threshold is user-specified.

24. The system in claim 21, wherein the one or more sets of program instructions are further configured to cause the one or more processors to:

provide one or more control signals to at least one process tool to improve performance of one or more fabrication processes, wherein the one or more control signals are generated based on the at least one excursion.

25. A method, comprising:

applying filtering to a semiconductor wafer map;

separating the filtered semiconductor wafer map into a plurality of dies;

generating a set of die comparison statistics for the plurality of dies;

generating at least one excursion map by applying at least one inspection threshold to the set of die comparison statistics; and detecting at least one excursion within the at least one excursion map.

26. The method in claim 25, wherein the at least one inspection threshold is established based on the set of die comparison statistics.

27. The method in claim 25, wherein the at least one inspection threshold is user-specified.

28. The method in claim 25, further comprising:

providing one or more control signals to at least one process tool to improve performance of one or more fabrication processes, wherein the one or more control signals are generated based on the at least one excursion.

* * * * *